Figure 1:
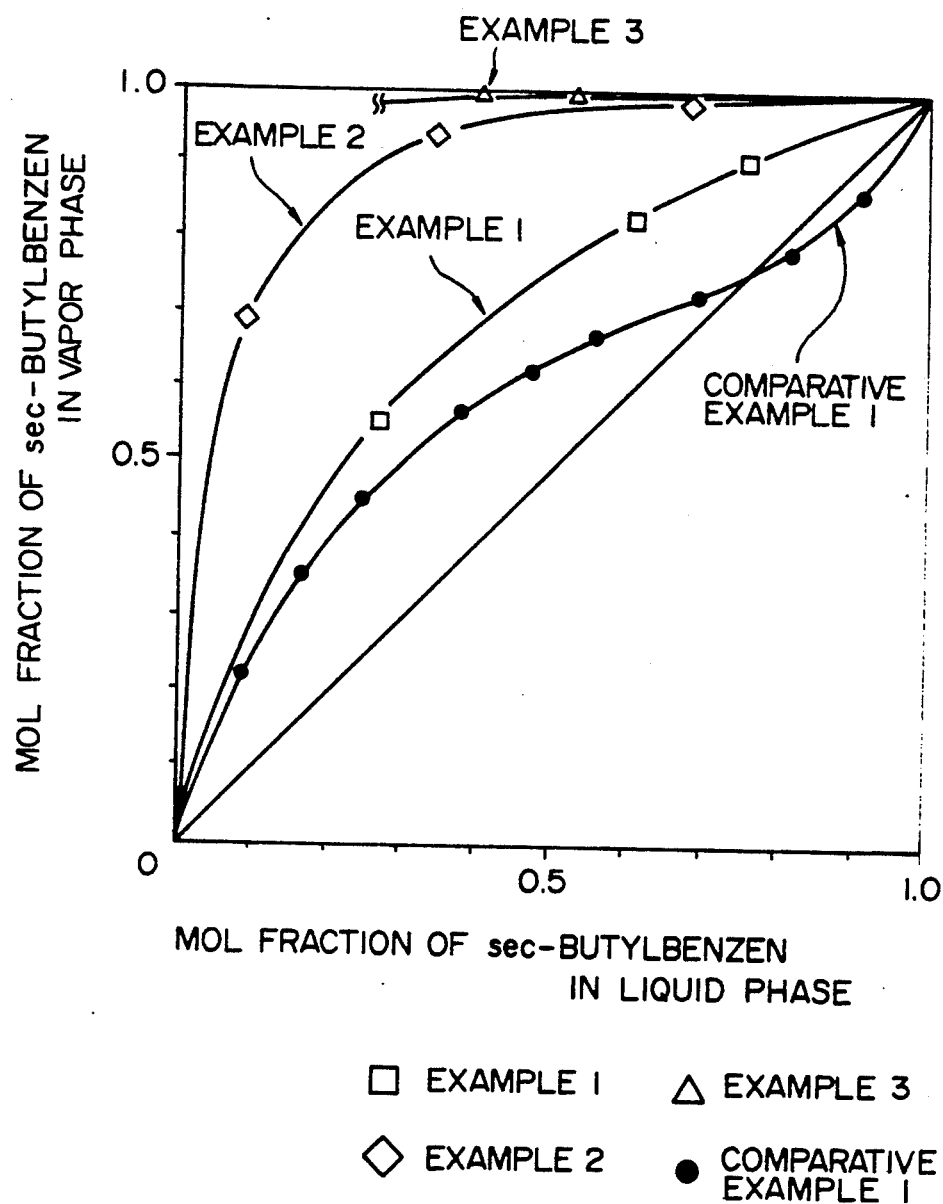

United States Patent [19]

Kogure et al.

[11] Patent Number: 5,334,774
[45] Date of Patent: Aug. 2, 1994

[54] PROCESS FOR PURIFYING PHENOL

[75] Inventors: Kayoko Kogure, Sodegaura; Kayoko Kogure, Ichihara; Michihiro Kawasaki, Ichihara; Masaaki Toma, Ichihara; Eiji Imamura, Kobe, all of Japan

[73] Assignee: Sumitomo Chemical Company, Limited, Osaka, Japan

[21] Appl. No.: 64,982

[22] Filed: May 24, 1993

[30] Foreign Application Priority Data

Jun. 5, 1992 [JP] Japan .................................. 4-145326
Oct. 6, 1992 [JP] Japan .................................. 4-267191
Dec. 16, 1992 [JP] Japan .................................. 4-335763

[51] Int. Cl.$^5$ ........................................ C07C 37/74
[52] U.S. Cl. ............................ 568/754; 568/749
[58] Field of Search ................. 568/750, 754, 749

[56] References Cited

U.S. PATENT DOCUMENTS 5,064,507 11/1991 O'Donnell et al. ................ 568/754

FOREIGN PATENT DOCUMENTS 0028522 5/1981 European Pat. Off. ............ 568/754
36-5713 4/1957 Japan .
48-80524 10/1973 Japan .
50-1258 1/1975 Japan .

Primary Examiner—Werren B. Lone
Attorney, Agent, or Firm—Cushman, Darby & Cushman

[57] ABSTRACT

A process for purifying and recovering phenol present in a mixed solution containing phenol and one or more compounds capable of forming azeotropic mixtures with phenol wherein an additive which is at least one compound belonging to the following groups 1 to 5 is added to the mixed solution and the resulting mixture is distilled:

group 1: dialkylene glycols having 2-10 carbon atoms, polyalkylene glycols having 2-10 carbon atoms, and the ethers thereof,
group 2: alkanediols having 2-20 carbon atoms,
group 3: ethanolamine-type compounds represented by the formula (1) shown below,
group 4: lactam compounds represented by the formula (2) shown below,
group 5: quinoline, sulfolane, and N,N-dimethylimidazolidinone,

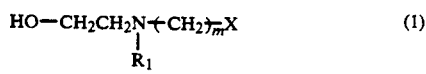

wherein $R_1$ represents an alkyl group having 1-6 carbon atoms, a cycloalkyl group having 1-6 carbon atoms, a monohydroxyalkyl group having 1-6 carbon atoms or a hydrogen atom, m represents an integer of 1-4, and X represents a hydroxyl group, an amino group or a hydrogen atom provided that $R_1$ and X may conjointly represent a group which can be formed by removing respectively one hydrogen atom from $R_1$ and X, respectively, and connecting the rests of $R_1$ and X to form a cyclic ring,

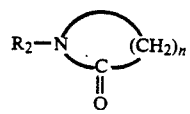

wherein $R_2$ represents an alkyl group having 1-6 carbon atoms, a cycloalkyl group having 1-6 carbon atoms, a monohydroxyalkyl group having 1-6 carbon atoms, or a hydrogen atom, and n represents an integer of 3-7.

18 Claims, 2 Drawing Sheets

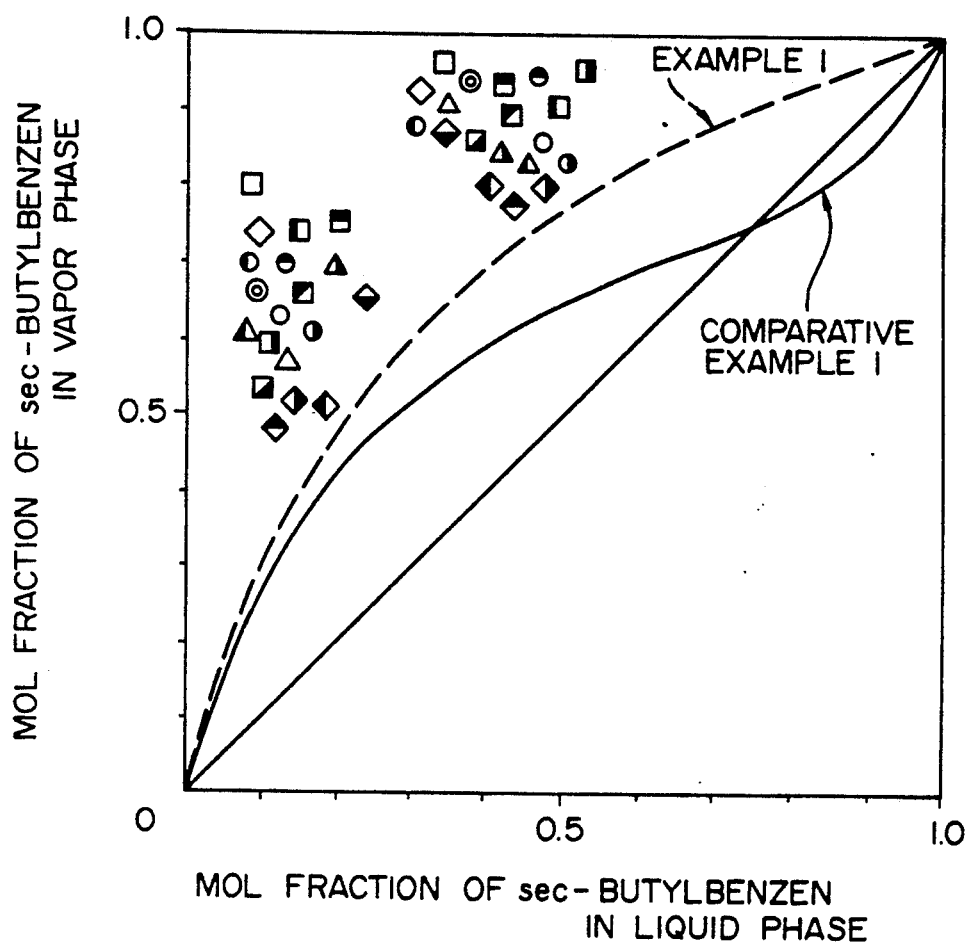

PROCESS FOR PURIFYING PHENOL

The present invention relates to a process for purifying phenol. In more particular, it relates to a process for purifying and recovering phenol from a mixture containing phenol and one or more components which will form azeotropic mixtures with phenol.

The process of the present invention is favorably used, for example, for purifying and recovering, from a decomposition liquid obtained by oxidizing sec-butylbenzene into sec-butylbenzene hydroperoxide and then decomposing the sec-butylbenzene hydroperoxide by acidic catalyst, phenol of the reaction product and unreacted sec-butylbenzene, respectively.

It is already known to the art to obtain phenol and methyl ethyl ketone by oxidizing sec-butylbenzene into sec-butylbenzene hydroperoxide and then decomposing the sec-butylbenzene hydroperoxide (Japanese Patent Kokai (Laid-open) JPA 48-80524). The decomposition liquid obtained by the above method contains phenol and methyl ethyl ketone, which are main reaction products, sec-butylbenzene, which is the starting material, and a large variety of by-products.

Sec-Butylbenzene of the starting material and phenol of the reaction product form an azeotropic mixture. Further, e.g. α,β-dimethylstyrene, α-ethylstyrene, acetophenone etc., which are by-products of the above-mentioned reaction, also form azeotropic mixtures with phenol. These azeotropic mixture-forming components cannot be separated completely from phenol by ordinary distillation. There has not been known a method which can separate and purify phenol efficiently from the decomposition liquid obtained by the above-mentioned process.

An object of the present invention is to provide a process for purifying and recovering phenol and sec-butylbenzene, respectively, from a liquid mixture containing phenol, sec-butylbenzene and one or more components which will form an azeotropic mixture with phenol efficiently.

Other objects and advantages of the present invention will become apparent from the detailed description to follow taken in conjunction with the appended claims.

According to the present invention, for the purpose of purifying and recovering phenol from a mixture containing phenol, sec-butylbenzene and one or more components which will form azeotropic mixtures with phenol, an additive which is at least one compound belonging to at least one group selected from the following groups 1-5 is added to the mixture and the resulting mixture is distilled:

group 1: dialkylene glycols having 2-10 carbon atoms, polyalkylene glycols having 2-10 carbon atoms, and the ethers thereof,
group 2: alkanediols having 2-10 carbon atoms,
group 3: ethanolamine-type compounds represented by the formula (1) shown below,
group 4: lactam compounds represented by the formula (2) shown below,
group 5: quinoline, sulfolane, and N,N-dimethylimidazolidinone,

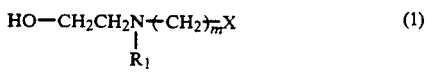   (1)

In the formula (1), $R_1$ represents an alkyl group having 1-6 carbon atoms, a cycloalkyl group having 1-6 carbon atoms, a monohydroxyalkyl group having 1-6 carbon atoms, or a hydrogen atom, m represents an integer of 1-4, and X represents a hydroxyl group, an amino group or a hydrogen atom. $R_1$ and X may conjointly represent a cyclic group which can be formed by removing respectively one hydrogen atom from $R_1$ and X, respectively, and connecting the rests of $R_1$ and X to form a ring.

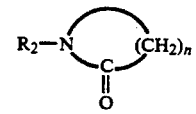   (2)

In the formula (2), $R_2$ represents an alkyl group having 1-6 carbon atoms, a cycloalkyl group having 1-6 carbon atoms, a monohydroxyalkyl group having 1-6 carbon atoms, or a hydrogen atom, and n represents an integer of 3-7.

According to the present invention, phenol can be purified, separated and recovered efficiently from the oxidation-decomposition reaction liquid obtained by using sec-butylbenzene as the starting material.

It is to be understood that the above description and the following detailed description of the invention are exemplary and explanatory only and are not restrictive of the invention as claimed.

FIG. 1 and FIG. 2 are diagrams showing the liquid-vapor equilibrium of phenol and sec-butylbenzene.

In the present invention, the components which form azeotropic mixtures with phenol include the compounds, e.g. sec-butylbenzene, α,β-dimethylstyrene, α-ethylstyrene, acetophenone etc.

At least one compound belonging to the above-mentioned groups 1-5 is used as the additive. Plural compounds which belong to the same group may be used. Plural compounds which belong to different groups may also be used.

Preferred among the groups are group 1, namely, dialkylene glycols having 2-10 carbon atoms, polyalkylene glycols having 2-10 carbon atoms, and ethers thereof, and group 2, namely, alkanediols having 2-20 carbon atoms.

Specific examples of the compound of the additive include diethylene glycol, diethylene glycol n-butyl ether, diethylene glycol isobutyl ether, diethylene glycol n-hexyl ether, triethylene glycol, 1,3-butanediol, 1,4-butanediol, 1,6-hexanediol, diethanolamine, N-methyldiethanolamine, triethanolamine, aminoethylethanolamine, cyclohexylpyrrolidinone, hydroxyethylpiperazine, hydroxylethylpyrrolidine, hydroxyethylpyrrolidinone, sulfolane, quinoline, and dimethylimidazolidinone. Preferred among them are diethylene glycol, triethylene glycol, 1,4-butanediol, 1,6-hexanediol, diethanolamine, N-methyldiethanolamine, triethanolamine, aminoethylethanolamine, cyclohexylpyrrolidinone, hydroxyethylpiperazine, hydroxylethylpyrrolidine, hydroxyethylpyrrolidinone, sulfolane, and dimethylimidazolidinone. More preferred are diethylene glycol, triethylene glycol, diethanolamine, hydroxylethylpyrrolidine, hydroxyethylpyrrolidinone, and dimethylimidazolidinone.

The amount of the additive to be used varies depending on conditions. In general, it is 10-100 parts by weight, preferably 20-80 parts by weight, relative to 10 parts by weight of phenol in the mixture. When the amount is too small, the separation of phenol from the components which form azeotropic mixtures with phenol is sometimes insufficient. On the other hand, addition of excessively large amount is economically disadvantageous.

According to the present invention as the mixture containing phenol and one or more components that will form azeotropic mixtures with phenol, a decomposition liquid which is obtained by oxidizing sec-butylbenzene to sec-butylbenzene hydroperoxide and then decomposing the sec-butylbenzene hydroperoxide may be used.

The mixture which is an oil layer obtained by neutralizing the decomposition liquid by aqueous alkaline solution or an oil layer obtained by washing that neutralized oil layer by water also may be used.

The weight ratio of phenol to sec-butylbenzene contained in the decomposition liquid is not particularly limited, but is usually from about 1:0.1 to about 1:10.

The decomposition liquid may contain components other than phenol and sec-butylbenzene. That is, the decomposition liquid contains methyl ethyl ketone, phenol and sec-butylbenzene of the main components, such by-products, e.g., $\alpha,\beta$-dimethylstyrene and $\alpha$-ethylstyrene, acetophenone, propiophenone, ketones, alcohols, hydrocarbons, dimers, polymers, tarry substances etc. Of these compounds, e.g. sec-butylbenzene, $\alpha,\beta$-dimethylstyrene, $\alpha$-ethylstyrene, acetophenone etc. form azeotropic mixtures with phenol, and it is very difficult to separate high purity phenol from these mixtures by usual distillation. According to the present invention, however, phenol of a high purity can be efficiently purified and recovered from such mixtures.

The method of distillation used is preferably extractive distillation, more preferably continuous extractive distillation. The extractive distillation may be either conducted after adding the additive to the material to be distilled or conducted while adding the additive to the distillation column. When the distillation is conducted while adding the additive, the additive is preferably fed to a stage higher than the feed stage of the distillation material. Further, the feed stage of the material and the feed stage of the additive are preferably apart from each other by a sufficient number of stages. The distillation pressure and distillation temperature may vary depending on the kind of the additive used, but are usually in the range of 0.1-1 kg/cm² (column top pressure) and 90°-250° C. (column top temperature).

In the process of the present invention, it is preferable to provide a step (A): separating components of low boiling points and a step (B): separating components of high boiling points. The overhead liquid obtained in the step (B) is preferably used as the mixture solution containing phenol and sec-butylbenzene.

In a preferred embodiment of the present invention, the low boiling point component separation step (A) is a step of subjecting a decomposition liquid, which is obtained by oxidizing sec-butylbenzene to sec-butylbenzene hydroperoxide and decomposing the sec-butylbenzene hydroperoxide, to distillation. According to this step, an overhead liquid containing methyl ethyl ketone as the main component and a bottom liquid containing phenol as the main component are obtained. The decomposition is performed by using a catalyst, preferably an acidic catalyst.

The high boiling point component separation step (B) is a step of subjecting the bottom liquid obtained in the step (A) to distillation. According to this step, an overhead liquid containing phenol and sec-butylbenzene as the main component and additionally containing the compounds, e.g. $\alpha,\beta$-dimethylstyrene, $\alpha$-ethylstyrene, acetophenone etc., and a bottom liquid containing high boiling point components such as ketones, alcohols, various dimers and tarry materials are obtained.

The overhead liquid of the low boiling point component separation step (A) contains, in addition to methyl ethyl ketone, low boiling point components such as water. The bottom liquid of the step (A) contains, besides phenol, high boiling point components, e.g. sec-butylbenzene, $\alpha,\beta$-dimethylstyrene, $\alpha$-ethylstyrene, acetophenone etc.

The distillation conditions in the step (A) may be, for example, a column top pressure of 500-1,000 torr and a column top temperature of 50°-140° C., through they may vary depending on the composition of the decomposition liquid to be distilled.

The distillation conditions in the high boiling point component separation step (B) are, for example, a column top pressure of 50-700 tort and a column top temperature of 30°-200° C., though they may vary depending on the composition of the liquid to be distilled.

In consideration of the efficiency, ketones and alcohols which have boiling points higher than that of acetophenone, e.g. propiophenone, are preferably removed as much as possible in the form of bottom liquid in the step of (B). Further, the alcohols contained in the decomposition liquid react with phenol and form a variety of dimers, so that it is not desirable to keep phenol and alcohols together at a high temperature for a long time. On the other hand, since the decomposition liquid contains high boiling point components such as tarry components, the column bottom temperature in the high boiling point component separation step (B) can become considerably high. In the step (B), therefore, plural distillation columns; preferably two distillation columns, different in operating pressure are preferably used. Ketones and alcohols having higher boiling points than acetophenone can be removed more easily and further the recovery of phenol can be improved by this embodiment. In the first distillation column, the column top pressure is set at about 400-800 torr. 40-80 parts by weight of phenol out of 100 parts by weight of phenol contained in the feed liquid and components having lower boiling points than phenol are distilled out of the column top, and the bottom liquid is fed to the second distillation column. In the second distillation column, the column top pressure is set at about 50-300 torr, the remaining phenol and acetophenone are distilled out of the column top and this distillate is recycled to the first distillation column. The overhead liquid from the first distillation column is fed to the above mentioned extractive distillation column.

The decomposition liquid from which high boiling point components like tar have been removed in the high boiling point component separation step (B), or the decomposition liquid from which low boiling point components have been further removed in the low boiling point component separation step (A), contains mainly phenol and sec-butylbenzene and further contains the compounds, e.g. $\alpha,\beta$-dimethylstyrene $\alpha$-ethylstyrene, acetophenone etc.. These components form azeotropic mixture with phenol, however they can be efficiently separated by extractive distillation of the present invention.

In the present invention, furthermore, phenol of a still higher purity can be obtained by using the following steps in combination with step (C).

Extractive distillation step (C): a step of adding the above-mentioned additive to the overhead liquid containing phenol and sec-butylbenzene as the main components obtained in the step (B) and distilling the resulting liquid to obtain an overhead liquid containing sec-butylbenzene as the main component and a bottom liquid containing phenol and the additive. The overhead liquid additionally contains compounds capable of forming azeotropic mixtures with phenol (e.g. $\alpha,\beta$-dimethylstyrene, $\alpha$-ethylstyrene, acetophenone, etc.).

Additive separation step (D): a step of subjecting the bottom liquid obtained in the step (C) to distillation to obtain from the column top an overhead liquid containing phenol as the main component and from the column bottom a bottom liquid containing the additive as the main component, and recycling the bottom liquid to the extractive distillation step (C).

Phenol purification step (E): a step of subjecting the overhead liquid of the step (D) to distillation to obtain high purity phenol.

Styrenes contained in the overhead liquid of the extractive distillation step (C), e.g., $\alpha,\beta$-dimethylstyrene and $\alpha$-ethylstyrene, can be converted into sec-butylbenzene by a method known to the art, for example, by hydrogenation. By recycling the sec-butylbenzene thus formed to a oxidation step of converting sec-butylbenzene into sec-butylbenzene hydroperoxide, effective utilization of styrenes can be attained. It is preferable to distill out nearly the whole of the styrenes, contained in the liquid subjected to the extractive distillation, into the overhead liquid of the extractive distillation step (C).

As to acetophenone, it is possible to distil out the whole amount of acetophenone contained in the mixed solution fed to the extractive distillation step (C) into the overhead liquid. The amount of acetophenone contained in the decomposition liquid fed to the step (C) varies depending on the conditions of oxidation and decomposition. As the amount of acetophenone increases, a larger amount of the additive is required. Therefore, when the load and economical efficiency of the extractive distillation column are taken into consideration, acetophenone is preferably recovered divided into the overhead liquid and the bottom liquid of the extractive distillation. The division is preferably conducted in such a proportion that, out of 100 parts by weight of total acetophenone contained in the decomposition liquid fed to the extractive distillation step (C), 30-100 parts by weight are contained in the overhead liquid of the step (C) and the remaining 0-70 parts by weight are contained in the bottom liquid of the step (C). The distillation pressure and distillation temperature may vary depending on the kind of additive of the step (C).

In the additive separation step (D), the bottom liquid obtained in the extractive distillation step (C) is subjected to distillation to obtain an overhead liquid containing phenol as the main component from the column top and a bottom liquid containing the additive as the main component from the column bottom. The bottom liquid is recycled to the extractive distillation step (C). Though the bottom liquid can be recycled as such to the extractive distillation step (C), the liquid may also be once subjected to distillation to remove impurities such as polymers and then recycled to the extractive distillation step (C).

The crude phenol recovered as the overhead liquid of the additive separation step (D) usually contains such impurities as acetophenone and various dimers. In order to remove these impurities, two phenol purification steps ($E_1$ and $E_2$) described below are preferably provided.

The first phenol purification step ($E_1$): a step of subjecting the overhead liquid of the additive separation step (D) to distillation to obtain an overhead liquid containing phenol as the main component and a bottom liquid containing the main component compounds having higher boiling points than phenol.

The second phenol purification step ($E_2$): a step of subjecting the overhead liquid of the first phenol purification step ($E_1$) to distillation to obtain an overhead liquid containing as the main components compounds having lower boiling points than phenol and a bottom liquid consisting essentially of high purity phenol.

It is also allowable that components having lower boiling points than phenol are removed first and then components having higher boiling points than phenol are removed. It is further allowable that the purification step is conducted in a single distillation column to remove components having lower boiling points than phenol from the column top and components having higher boiling points than phenol from the column bottom, and to recover high purity phenol from the middle stage of the distillation column.

Acetophenone divided to the column bottom in the extractive distillation step (C) will be contained in the bottom liquid of the first phenol purification step ($E_1$). Since the bottom liquid of the step ($E_1$) also contains phenol, which is capable of forming an azeotropic mixture with acetophenone, the liquid is preferably recycled to any desired step from the decomposition step to the extractive distillation step (C), whereby the recovery of phenol can be improved.

The following examples are provided to illustrate and are in no way intended to limit the invention.

EXAMPLE

The present invention will be described in more detail below with reference to Examples and Comparative Examples.

The degree of separation of two components by distillation may be expressed by vapor-liquid equilibriums, which is conveniently handled with an x-y diagram.

An x-y diagram in a graph obtained by plotting the mol fraction (y) in the vapor phase of a low boiling point component versus the mol fraction (x) thereof in the liquid phase. The more convex upwards the x-y diagram is against the straight line y=x, the better the two components can be separated. When the x-y diagram is near to the straight line y=x, the two components can be difficultly separated. That is, the more upwards from the straight line y=x, the x-y diagram is plotted, the better the two components can be separated. When the straight line y=x and the x-y diagram intersect each other, an azeotropic mixture is formed at the composition corresponding to the point of intersection, so that the two components cannot be separated by ordinary distillation.

The measure of efficiency of separation by distillation generally used is relative volatility ($\alpha$). In the preferred embodiment of the present invention, the term relative volatility means the ratio of the volatility of sec-butylbenzene to that of phenol. The nearer to 1 the value is, the more difficult the separation is. With the increase of the value, phenol and sec-butylbenzene become more easily separable. The value of α at the azeotropic composition is 1.0. Though, in the Examples, determination was made of the vapor-liquid equilibrium of a three component system to which an additive had been added in addition to sec-butylbenzene and phenol, the α value and the plot on the x-y diagram were determined based on the molar ratio of the two components, sec-butylbenzene and phenol.

EXAMPLE 1

To a mixed solution (40 g) of sec-butylbenzene and phenol was added diethylene glycol (20 g) as the additive and the vapor-liquid equilibrium was determined with the resulting mixture. Three kinds of mixed solutions prepared so as to have compositions of molar ratios of sec-butylbenzene to phenol of 30 to 70, 70 to 30 and 80 to 20, respectively, were used as the above-mentioned mixed solution of sec-butylbenzene and phenol. The apparatus used for the determination was an Othmer-type equilibrium distillation apparatus. The determination pressure was 150 mmHg. The results of determination are shown in FIG. 1 and Table 1.

EXAMPLES 2 AND 3

In the same manner as in Example 1, diethylene glycol was added as the additive to a mixed solution (40 g) of sec-butylbenzene and phenol in such a proportion that the weight ratio of the mixed solution of sec-butylbenzene and phenol to the additive might be 1 to 1 and 1 to 2, and the vapor-liquid equilibrium was determined. The mixed solution of sec-butylbenzene and phenol was prepared in the compositions shown in Table 1. The results of determination are shown in FIG. 1 and Table 1.

COMPARATIVE EXAMPLE 1

The vapor-liquid equilibrium of sec-butyl benzene-phenol in the absence of an additive was determined. Mixed solutions were prepared such that the molar ratio of sec-butylbenzene to phenol might be 10:90 to 90:10, and vapor-liquid equilibrium was determined with the solutions at a pressure of 150 mmHg by using an Othmer-type vapor-liquid equilibrium distillation apparatus. The results are shown in FIG. 1.

The x-y diagram intersects the straight line y=x at a mol fraction of sec-butylbenzene of 0.75. That is, an azeotropic mixture is formed at a molar ratio of sec-butylbenzene to phenol of 75 to 25, so that it is impossible to concentrate sec-butylbenzene to concentrations of 75% by mol or more.

On the other hand, as in Examples 1 to 3, when an additive is added, the x-y diagram does not intersect the line y=x and forms a curve convex upwards. In other words, the azeotrope of sec-butylbenzene and phenol can be eliminated completely, and the separation of sec-butylbenzene from phenol becomes possible. As the amount of the additive increases, the x-y diagram comes to be plotted more upwards relative to the line y=x, and the separation of sec-butylbenzene from phenol becomes easier. This is evident also from the fact that the value of α increases with the increase of the added amount of that.

EXAMPLES 4 TO 21

To mixed solutions (30 g) of sec-butylbenzene and phenol were added the additive (30 g each) shown in Table 2, and liquid-vapor equilibrium was determined with an Othmer-type liquid-vapor equilibrium distillation apparatus at a pressure of 150 mmHg. The mixed solutions were prepared such that the molar ratio of sec-butylbenzene to phenol might be 20 to 80 and 50 to 50. The results of determination were plotted in FIG. 2.

Table 2 shows the values of α at respective compositions with each of the additives. It can be said that the higher α value an additive gives, the better separation efficiency is provided.

FIG. 2 reveals that the vapor-liquid equilibrium of sec-butylbenzene and phenol in the presence of an additive is plotted above the x-y diagram obtained in the absence of an additive, showing an easier separation of sec-butylbenzene from phenol.

Further, since the x-y diagrams of the present Examples are plotted at upper parts as compared with the x-y diagram of Example 1 wherein azeotropic has been completely eliminated, the separation efficiency in the present Examples is higher than in Example 1. In other words, by using any of the additives, it becomes possible to eliminate that azeotrope of sec-butylbenzene and phenol and to separate the two components with good efficiency.

EXAMPLE 22

A liquid mixture consisting essentially of 49.5% by weight of sec-butylbenzene, 44.6% by weight of phenol, 4.8% by weight of acetophenone and 1.1% by weight of other ketones was subjected to extractive distillation using diethylene glycol as the additive. The distillation was continuous distillation at a pressure of 150 mmHg. The above-mentioned liquid mixture was fed to the distillation column at a rate of 300 g per hour, and diethylene glycol was fed into the column at a rate of 900 g per hour at a stage positioned higher than the feed port of the liquid mixture. The distribution factor to the column top and the column bottom of the respective components determined from the compositions of the overhead liquid and the bottom liquids are as shown in Table 3. The distribution factors of sec-butylbenzene and acetophenone were both 100% to the column top side, and the distribution factor of phenol to the column top side was 0%. Thus, sec-butylbenzene and acetophenone could be completely separated from phenol.

COMPARATIVE EXAMPLE 2

The experimental procedures were essentially the same as described in Example 22 with the exception that diethyleneglycol of the additive was not used. The distribution factors of the respective components to the column top and the column bottom determined from the compositions of the overhead liquid and the bottom liquid are as shown in Table 4. The distribution factor of phenol to the column top side was 21%, and thus complete separation could not be attained unlike in Example 22.

EXAMPLE 23

From a decomposition liquid obtained by oxidizing sec-butylbenzene to sec-butylbenzene hydroperoxide and then subjecting the hydroperoxide to decomposition using sulfuric acid, followed by neutralization with an aqueous alkaline solution, were distilled off such the low boiling point components as methyl ethyl ketone, step (A), and were further distilled off such the high boiling point components as ketones, alcohols, dimers of alcohols and resinous components, step (B). Then a liquid mixture containing 6.1% by weight of methyl ethyl ketone, 45.6% by weight of sec-butylbenzene, 41.9% by weight of phenol, 4.0% by weight of acetophenone, 1.0% by weight of α,β-dimethylstyrene, and 0.2% by weight of α-ethylstyrene was obtained. This liquid mixture was subjected to extractive distillation, step (C), using diethylene glycol. The distillation was conducted by continuous distillation at a pressure of 150 mmHg. The above-mentioned liquid mixture was fed to the distillation column at a rate of 620 g per hour and, from the stage positioned higher than the feed port of the liquid mixture, diethylene glycol was fed into the column at a rate of 1,840 g per hour. The distribution factors of the respective components to the column top and the column bottom determined from the compositions of the overhead liquid and the bottom liquid are as shown in Table 5.

EXAMPLE 24

A decomposition liquid was obtained by oxidizing sec-butylbenzene to sec-butylbenzene hydroperoxide, and then subjecting the hydroperoxide to decomposition using sulfuric acid as the catalyst. The decomposition liquid was neutralized with an aqueous alkaline solution and then separated into an oil layer and an aqueous layer. Then a solution was obtained, as the neutralized decomposition oil layer, which comprised 22.3% by weight of methyl ethyl ketone, 25.8% by weight of sec-butylbenzene, 30.9% by weight of phenol, 11.0% by weight of acetophenone, 2.7% by weight of dimethylstyrenes (α,β-dimethylstyrene and α-ethylstyrene), 0.5% by weight of phenol-alcohol dimer and 2.8% by weight of water. The solution was fed at a rate of 8.0 kg per hour to a distillation column filled with regular packing and distilled at a column top pressure of 760 Torr and a column top temperature of 75° C. Methyl ethyl ketone, water, and impurities associated therewith were distilled out as the overhead liquid, and a liquid containing 34.2% by weight of sec-butylbenzene, 41.3% by weight of phenol, 15.1% by weight of acetophenone, and 3.5% by weight of dimethylstyrenes was obtained as the bottom liquid (step (A)).

The bottom liquid obtained above was then fed at a rate of 5.4 kg per hour to a distillation column and distilled at a column top pressure of 195 Torr and a column top temperature of 133° C. High boiling point compounds including heavy tarry components, and dimers of phenol and various alcohols were removed as the bottom liquid, and the solution containing 36.9% by weight of sec-butylbenzene, 43.3% by weight of phenol, 13.3% by weight of acetophenone, and 3.8% by weight of dimethylstyrenes was obtained as the overhead liquid (step (B)).

Subsequently, the overhead liquid obtained above was fed from a lower stage of the extractive distillation column at a rate of 4.0 kg per hour, simultaneously diethylene glycol was fed from an upper stage of the extractive distillation column at a rate of 5.6 kg per hour, and extractive distillation was conducted at a column top pressure of 300 Torr and a column top temperature of 140° C. Resultantly, a solution containing sec-butylbenzene, dimethylstyrenes and acetophenone was distilled out as the overhead liquid, and a solution containing 22.1% by weight of phenol, 4.4% by weight of acetophenone, and 72.7% by weight of diethylene glycol was obtained as the bottom liquid. The concentrations of sec-butylbenzene and dimethylstyrenes in the bottom liquid were 200 ppm or less. A proportion of 63% by weight of acetophenone was recovered from the column bottom relative to its total amount contained in the liquid fed to the distillation column (step (C)).

Then, the bottom liquid obtained in the above step was fed at a rate of 6.0 kg per hour to a distillation column and distilled at a column top pressure of 300 Torr and a column top temperature of 157° C. Diethylene glycol as the additive was separated to the column bottom and an overhead liquid containing 82.3% by weight of phenol and 16.0% by weight of acetophenone was obtained from the column top (step (D)).

The overhead liquid obtained in the above-mentioned step was fed at a rate of 7.0 kg per hour to a distillation column and distilled at a column top pressure of 300 Torr and a column top temperature of 151° C. Acetophenone was removed from the column bottom, and a solution containing 99.89% by weight of phenol was obtained from the column top (step ($E_1$)). The bottom liquid contained phenol associated with acetophenone and high boiling point ketones and alcohols. The overhead liquid contained, besides phenol, such impurities as sec-butylbenzene and dimethylstyrenes respectively in a very small amount.

Finally, the overhead liquid obtained in the above step was fed at a rate of 5.5 kg per hour to a distillation column and distilled at a column top pressure of 330 Torr and a column top temperature of 152° C. Phenol of a high purity of 99.99% by weight or more was obtained from the column bottom (step ($E_2$)). The phenol thus obtained had a quality which fully meets the JIS specification for reagent grade phenol.

TABLE 1

| Example No. | Mixed solution:additive (wt. ratio) | Mixed solution composition*[1] | α |
|---|---|---|---|
| 1 | 1:0.5 | 30/70 | 3.5 |
|   |   | 70/30 | 3.3 |
|   |   | 80/20 | 3.6 |
| 2 | 1:1 | 20/80 | 23.2 |
|   |   | 50/50 | 22.5 |
|   |   | 75/25 | 8.6 |
| 3 | 1:2 | 50/50 | 39.0 |
|   |   | 70/30 | 23.5 |

Note:
*[1]Molar ratio of sec-butylbenzene to phenol

TABLE 2

|   |   | α | |
|---|---|---|---|
|   | Additive (group number) | 20/80*[2] | 50/50*[3] |
| Example 2 | Diethylene glycol (1) | 23.2 | 22.5 |
| Example 4 | Diethylene glycol n-butyl ether (1) | 6.6 | 6.6 |
| Example 5 | Diethylene glycol isobutyl ether (1) | 4.5 | 5.7 |
| Example 6 | Diethylene glycol n-hexyl ether (1) | 5.6 | 4.7 |
| Example 7 | Triethylene glycol (1) | 4.8 | 15.8 |
| Example 8 | 1,3-Butanediol (2) | 13.2 | 8.3 |
| Example 9 | 1,4-Butanediol (2) | 9.5 | 17.1 |
| Example 10 | 1,6-Hexanediol (2) | 9.4 | 12.2 |
| Example 11 | Diethanolamine (3) | 35.5 | 32.8 |
| Example 12 | N-Methyldiethanolamine (3) | 9.1 | 14.3 |
| Example 13 | Triethanolamine (3) | 11.6 | 16.6 |
| Example 14 | Aminoethylethanolamine (3) | 9.7 | 16.7 |
| Example 15 | Hydroxylethylpyrrolidine (3) | 14.0 | 12.6 |
| Example 16 | Hydroxyethylpiperazine (3) | 9.9 | 21.2 |

TABLE 2-continued

| | Additive (group number) | α 20/80*2 | 50/50*3 |
|---|---|---|---|
| Example 17 | Cyclohexylpyrrolidinone (4) | 9.4 | 10.6 |
| Example 18 | Hydroxyethylpyrrolidinone (4) | 14.6 | 27.4 |
| Example 19 | Sulfolane (5) | 17.0 | 16.4 |
| Example 20 | Quinoline (5) | 8.2 | 6.4 |
| Example 21 | Dimethylimidazolidinone (5) | 14.4 | 22.8 |
| Comp. Example 1 | None | 4.0 | 1.9 |

Note:
*2Molar ratio of sec-butylbenzene/phenol = 20/80
*3Molar ratio of sec-butylbenzene/phenol = 50/50

TABLE 3

(Example 22)

| | Distribution factor (%) | |
|---|---|---|
| | Top | Bottom |
| Methyl ethyl ketone | 100 | 0 |
| sec-Butylbenzene | 100 | 0 |
| Phenol | 0 | 100 |
| Acetophenone | 100 | 0 |
| Diethylene glycol | 0 | 100 |

TABLE 4

(Comparative Example 2)

| | Distribution factor (%) | |
|---|---|---|
| | Top | Bottom |
| sec-Butylbenzene | 100 | 0 |
| Phenol | 21 | 79 |
| Acetophenone | 0 | 100 |
| Other ketones | 0 | 100 |

TABLE 5

(Example 23)

| | Distribution factor (%) | |
|---|---|---|
| | Top | Bottom |
| Methyl ethyl ketone | 100 | 0 |
| sec-Butylbenzene | 100 | 0 |
| Phenol | 0 | 100 |
| Acetophenone | 99 | 1 |
| α,β-Dimethylstyrene | 100 | 0 |
| α-Ethylstyrene | 100 | 0 |
| Diethylene glycol | 0 | 100 |

What is claimed is:

1. A process for purifying and recovering phenol from a reaction liquid produced by oxidizing sec-butylbenzene to sec-butylbenzene hydroperoxide and decomposing the resulting sec-butylbenzene hydroperoxide to phenol and methyl ethyl ketone, which process comprises the steps of:

(A) distilling the reaction liquid to obtain a first overhead liquid mainly containing methyl ethyl ketone from the top of a distillation column, and a first bottom liquid mainly containing phenol and unreacted sec-butylbenzene from the bottom of the distillation column;

(B) distilling the first bottom liquid to obtain a second overhead liquid mainly containing phenol, sec-butylbenzene and other materials which form an azeotropic mixture with phenol from the top of the distillation column, and a second bottom liquid containing materials having higher boiling points than that of phenol from the bottom of the distillation column; and (C) distilling the second overhead liquid in the presence of an additive selected from the following groups 1 to 5:

group 1: dialkylene glycols having 2-10 carbon atoms, polyalkylene glycols having 2-10 carbon atoms, and the ethers thereof;

group 2: alkanediols having 2-20 carbon atoms;

group 3: ethanolamine-type compounds represented by the formula (1)

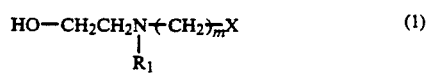

wherein $R_1$ represents an alkyl group having 1-6 carbon atoms, a cycloalkyl group having 3-6 carbon atoms, a monohydroxyalkyl group having 1-6 carbon atoms or a hydrogen atom, m represents an integer of 1-4, and X represents a hydroxyl group, an amino group or a hydrogen atom, provided that $R_1$ and X can conjointly represent a cyclic group formed by removing one hydrogen atom from $R_1$ and X, respectively, and connecting $R_1$ and X to form a ring;

group 4: lactam compounds represented by the formula (2)

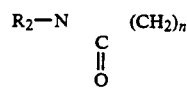

wherein $R_2$ represents an alkyl group having 1-6 carbon atoms, a cycloalkyl group having 3-6 carbon atoms, a monohydroxyalkyl group having 1-6 carbon atoms, or a hydrogen atom, and n represents an integer of 3-7; and group 5: quinoline, sulfolane and N,N-dimethylimidazolidinone, to obtain a third overhead liquid containing sec-butylbenzene and other materials which form an azeotropic mixture with phenol from the top of the distillation column, and a third bottom liquid containing phenol and the additive from the bottom of the distillation column;

(D) distilling the third bottom liquid to obtain a fourth overhead liquid mainly containing phenol from the top of the distillation column and a fourth bottom liquid containing the additive from the bottom of the distillation column; and (E) distilling the fourth overhead liquid to obtain purified phenol.

2. The process according to claim 1, wherein the step B further comprises:

(B1) distilling the first bottom liquid obtained in the step (A) to obtain the second overhead liquid mainly containing phenol, sec-butylbenzene and other materials which form an azeotropic mixture with phenol from the top of the distillation column, and the second bottom liquid containing phenol and the materials having higher boiling points than that of phenol from the bottom of the distillation column;

(B2) distilling the second bottom liquid obtained in the step B1 to obtain a fifth overhead liquid mainly containing phenol and acetophenone from the top of the distillation column; and (B3) recycling the fifth overhead liquid to the step B1; the step D further comprises:

(D2) recycling the fourth bottom liquid containing the additive obtained in the step D is recycled to the step C; and the step E further comprises:

(E1) distilling the fourth overhead liquid obtained in the step (D) to obtain a sixth overhead liquid mainly containing phenol and a sixth bottom liquid containing materials having higher boiling points than phenol; and (E2) distilling the sixth overhead liquid of step E1 to obtain purified phenol as a seventh bottom liquid and materials having lower boiling points than phenol as a seventh overhead liquid.

3. The process according to claim 2, wherein the sixth bottom liquid obtained in the step E1 which contains phenol and acetophenone is recycled to any of the preceding steps from the decomposition step to the step C.

4. The process according to claim 1, wherein said other materials which form an azeotropic mixture with phenol contained in the second overhead liquid of the step B are α, β-dimethylstyrene, α-ethylstyrene and acetophenone.

5. The process according to claim 1, wherein the weight ratio of phenol to the additive is 1/1 to 1/10.

6. The process according to claim 5, wherein the weight ratio of phenol to the additive is ½ to ⅕.

7. The process according to claim 2 wherein, out of 100 parts by weight of the acetophenone, 30 to 100 parts by weight is made to be contained in the third overhead liquid of the step C and the remaining 70 to 0 parts is made to be contained in the third bottom liquid of the step C and recovered from the step E or E1 as the mixture of phenol and acetophenone and recycled to any step from the decomposition step to the step C.

8. The process according to claim 1, which further comprises the steps of distilling the bottom liquid from the step D to obtain the purified additive and recycling the additive to the step C.

9. The process according to claim 1, which further comprises a step of converting α,β-dimethylstyrene, αethylstyrene contained in the overhead liquid of the step C into sec-butylbenzene and recycling it as a starting material.

10. A process for purifying and recovering phenol from a reaction liquid produced by oxidizing sec-butylbenzene to sec-butylbenzene hydroperoxide and decomposing the resulting sec-butylbenzene hydroperoxide to phenol and methyl ethyl ketone, which process comprises the steps of:

(A) distilling the reaction liquid to obtain a first overhead liquid mainly containing methyl ethyl ketone from a top of a distillation column, and a first bottom liquid mainly containing phenol and unreacted sec-butylbenzene from the bottom of the distillation column;

(B) distilling the first bottom liquid to obtain a second overhead liquid mainly containing phenol, sec-butylbenzene and other materials which form an azeotropic mixture with phenol from the top of the distillation column, and a second bottom liquid containing the materials having higher boiling points than that of phenol from the bottom of the distillation column;

(C) distilling the second overhead liquid in the presence of an additive selected from the groups 2 to 5;

group 2: alkanediols having 2-20 carbon atoms;
group 3: ethanolamine-type compounds represented by the formula (1)

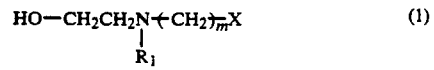

wherein $R_1$ represents an alkyl group having 1-6 carbon atoms, a cycloalkyl group having 3-6 carbon atoms, a monohydroxyalkyl group having 1-6 carbon atoms or a hydrogen atom, m represents an integer of 1-4, and X represents a hydroxyl group, an amino group or a hydrogen atom, provided that $R_1$ and X can conjointly represent a cyclic group formed by removing one hydrogen atom from $R_1$ and X, respectively, and connecting $R_1$ and X to form a ring;

group 4: lactam compounds represented by the formula (2)

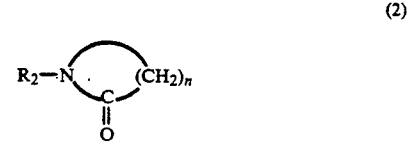

wherein $R_2$ represents an alkyl group having 1-6 carbon atoms, a cycloalkyl group having 3-6 carbon atoms, an monohydroxyalkyl group having 1-6 carbon atoms, or a hydrogen atom, and n represents an integer of 3-7; and group 5: quinoline, sulfolane and N,N-dimethylimidazolidinone, to obtain a third overhead liquid containing sec-butylbenzene and other materials which form an azeotropic mixture with phenol from the top of the distillation column, and a third bottom liquid containing phenol and the additive from the bottom from the distillation column;

(D) distilling the third bottom liquid to obtain a fourth overhead liquid mainly containing phenol from the top of the distillation column and a fourth bottom liquid containing the additive from the bottom of the distillation column; and (E) distilling the fourth overhead liquid to obtain purified phenol.

11. The process according to claim 10, wherein the step B further comprises:

(B1) distilling the first bottom liquid obtained in the step (A) to obtain the second overhead liquid mainly containing phenol, sec-butylbenzene and other materials which form an azeotropic mixture with phenol from the top of the distillation column, and the second bottom liquid containing phenol and the materials having higher boiling points than that of phenol from the bottom of the distillation column;

(B2) distilling the second bottom liquid obtained in the step B1 to obtain a fifth overhead liquid mainly containing phenol and acetophenone from the top of the distillation column; and (B3) recycling the fifth overhead liquid to the step B1; the step D further comprises:

(D2) recycling the fourth bottom liquid containing the additive obtained in the step D is recycled to the step C; and the step E further comprises:

(E1) distilling the fourth overhead liquid obtained in the step (D) to obtain a sixth overhead liquid mainly containing phenol and a sixth bottom liquid containing materials having higher boiling points than phenol; and (E2) distilling the sixth overhead liquid of step E1 to obtain purified phenol as a seventh bottom liquid and materials having lower boiling points than phenol as a seventh overhead liquid.

12. The process according to claim 11, wherein the sixth bottom liquid obtained in the step E1 which contains phenol and acetophenone is recycled to any of the preceding steps from the decomposition step to the step C.

13. The process according to claim 10, wherein said other materials which form an azeotropic mixture with phenol contained in the second overhead liquid of the step B are $\alpha,\beta$-dimethylstyrene, $\alpha$-ethylstyrene and acetophenone.

14. The process according to claim 10, wherein the weight ratio of phenol to the additive is 1/1 to 1/10.

15. The process according to claim 14, wherein the weight ratio of phenol to the additive is ½ to ¼.

16. The process according to claim 11 wherein, out of 100 parts by weight of the acetophenone, 30 to 100 parts by weight is made to be contained in the third overhead liquid of the step C and the remaining 70 to 0 parts is made to be contained in the third bottom liquid of the step C and recovered from the step E or E1 as the mixture of phenol and acetophenone and recycled to any step from the decomposition step to the step C.

17. The process according to claim 10, which further comprises the steps of distilling the bottom liquid from the step D to obtain the purified additive and recycling the additive to the step C.

18. The process according to claim 10, which further comprises a step of converting $\alpha,\beta$-dimethylstyrene, $\alpha$-ethylstyrene contained in the overhead liquid of the step C into sec-butylbenzene and recycling it as a starting material.

* * * * *

UNITED STATES PATENT AND TRADEMARK OFFICE
CERTIFICATE OF CORRECTION

PATENT NO. : 5,334,774
DATED : August 2, 1994
INVENTOR(S) : KOGURE et al

It is certified that error appears in the above-identified patent and that said Letters Patent is hereby corrected as shown below:

TITLE PAGE

Kindly change second inventor's name from "Kayoko Kogure" to --Kazuo Kimura--.

Signed and Sealed this

Fifth Day of September, 1995

Attest:

BRUCE LEHMAN

Attesting Officer

Commissioner of Patents and Trademarks